(12) United States Patent
Magnusson et al.

(10) Patent No.: US 10,426,667 B2
(45) Date of Patent: Oct. 1, 2019

(54) AUTOMATIC DARKENING FILTER APPARATUS AND METHOD

(71) Applicant: 3M INNOVATIVE PROPERTIES COMPANY, St. Paul, MN (US)

(72) Inventors: Kristina M. Magnusson, Djurmo (SE); Kenneth Jarefors, Borlänge (SE)

(73) Assignee: 3M Innovative Properties Company, St. Paul, MN (US)

( * ) Notice: Subject to any disclaimer, the term of this patent is extended or adjusted under 35 U.S.C. 154(b) by 127 days.

(21) Appl. No.: 15/543,352

(22) PCT Filed: Feb. 1, 2016

(86) PCT No.: PCT/US2016/015912
§ 371 (c)(1),
(2) Date: Jul. 13, 2017

(87) PCT Pub. No.: WO2016/126587
PCT Pub. Date: Aug. 11, 2016

(65) Prior Publication Data
US 2017/0367891 A1     Dec. 28, 2017

Related U.S. Application Data

(60) Provisional application No. 62/113,160, filed on Feb. 6, 2015.

(51) Int. Cl.
*A61F 9/06*     (2006.01)
*G02B 26/02*    (2006.01)
(Continued)

(52) U.S. Cl.
CPC .............. *A61F 9/061* (2013.01); *A61F 9/067* (2013.01); *B23K 9/095* (2013.01); *G02B 26/02* (2013.01);
(Continued)

(58) Field of Classification Search
CPC ....... A61F 9/061; A61F 9/067; H04N 5/2353; H04N 5/2351; G02B 26/02
See application file for complete search history.

(56) References Cited

U.S. PATENT DOCUMENTS 4,225,771 A    9/1980  Justice
4,620,322 A    11/1986 Eggenschwiler
(Continued)

FOREIGN PATENT DOCUMENTS

CA    2689701      1/2011
CN    101214178    7/2008
(Continued)

OTHER PUBLICATIONS

International Search Report for PCT International Application No. PCT/US2016/015912, dated May 24, 2016, 4 pages.
(Continued)

*Primary Examiner* — Tony Ko
(74) *Attorney, Agent, or Firm* — Kenneth B. Wood

(57) ABSTRACT

Automatic darkening filters are often provided on a protective headgear, where protection from high intensity light is desired. An automatic darkening filter includes a switchable shutter, a shutter control system, a light sensor, and an imaging acquisition device. The switchable shutter is capable of assuming at least a dark state, a light state and an intermediate state.

20 Claims, 2 Drawing Sheets

(51) Int. Cl.
*H04N 5/235* (2006.01)
*B23K 9/095* (2006.01)

(52) U.S. Cl.
CPC ......... *H04N 5/2351* (2013.01); *H04N 5/2353* (2013.01)

(56) References Cited

U.S. PATENT DOCUMENTS

| | | | |
|---|---|---|---|
| 4,698,484 | A | 10/1987 | Babcock |
| 5,275,327 | A | 1/1994 | Watkins |
| 5,302,815 | A | 4/1994 | Eggenschwiler |
| 5,530,572 | A | 6/1996 | He |
| 6,070,264 | A | 6/2000 | Hamilton |
| 6,710,298 | B2 | 3/2004 | Eriksson |
| 6,786,610 | B2 | 9/2004 | Faris |
| 8,331,001 | B2 | 12/2012 | Hsieh et al. |
| 8,416,355 | B2 | 4/2013 | Tamir et al. |
| 8,537,294 | B2 | 9/2013 | Sundell |
| 2005/0001155 | A1 | 1/2005 | Fergason |
| 2005/0133685 | A1 | 6/2005 | Hamilton |
| 2007/0056072 | A1 | 3/2007 | Steinemann |
| 2009/0231423 | A1 | 9/2009 | Becker |
| 2012/0291172 | A1* | 11/2012 | Wills ............... B23K 9/0956 2/8.2 |
| 2013/0128135 | A1 | 5/2013 | Sundell |
| 2013/0291271 | A1 | 11/2013 | Becker et al. |
| 2014/0215673 | A1 | 8/2014 | Lilenthal |

FOREIGN PATENT DOCUMENTS

| | | |
|---|---|---|
| EP | 0349665 | 1/1990 |
| EP | 0611286 | 8/1994 |
| EP | 2140964 | 1/2010 |
| GB | 2302412 | 1/1997 |
| JP | 11277231 | 10/1999 |
| KR | 2013-0090650 | 8/2013 |
| WO | WO 1984-01037 | 3/1984 |
| WO | WO 1985-01905 | 5/1985 |
| WO | WO 2005/008275 A1 | 1/2005 |
| WO | WO 2007-140642 | 12/2007 |
| WO | WO 2012-048436 | 4/2012 |

OTHER PUBLICATIONS

Extended European Search Report, Application No. EP16747051.7, dated Sep. 18, 2018, 3 pages.

* cited by examiner

AUTOMATIC DARKENING FILTER APPARATUS AND METHOD

BACKGROUND

Automatic darkening filters are often provided on protective headgear (e.g., headwear or eyewear), where protection from high intensity light is desired.

SUMMARY

In broad summary, herein is disclosed an automatic darkening filter comprising a switchable shutter, a shutter control system, a light sensor, and an imaging acquisition device. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Figure 1:
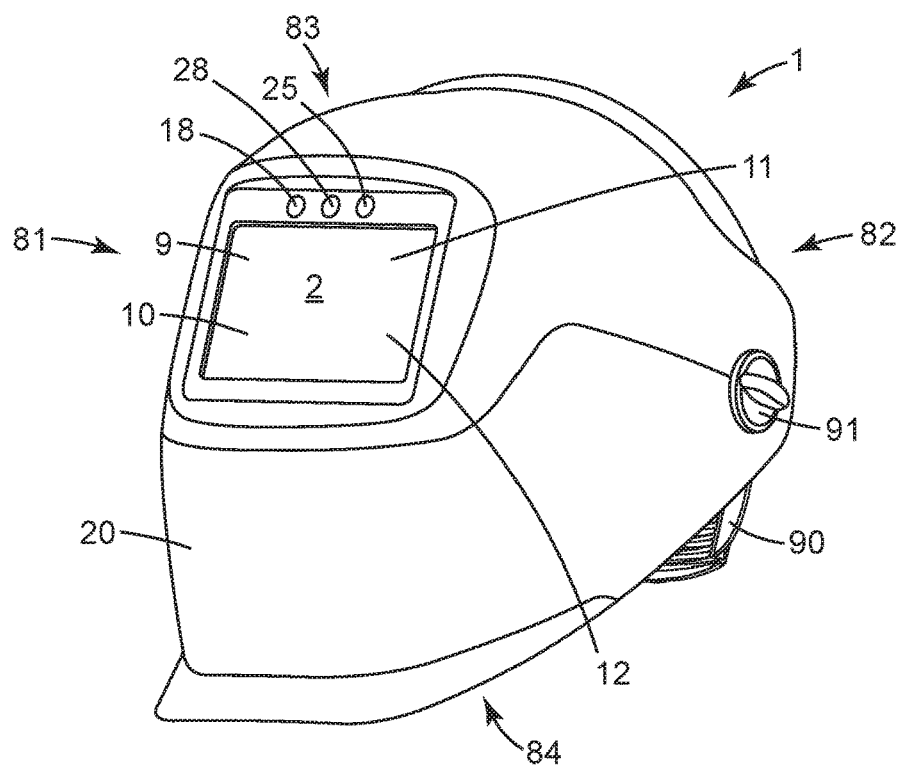
FIG. 1 is a front-side perspective view of an exemplary protective headgear comprising an exemplary automatic darkening filter mounted therein.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted.

DETAILED DESCRIPTION

Herein is disclosed an automatic darkening filter apparatus 10 configured to be mounted in a protective headgear 1. In various embodiments, protective headgear 1 may comprise e.g. a helmet, a shield, or a visor (e.g., a welding helmet, shield or visor), noting that there may not always be bright-line boundaries between protective headgear of these categories. As show in exemplary embodiment in FIGS. 1 and 2, exemplary protective headgear 1 comprises a main body 20 that (with headgear 1 as conventionally worn by a person) comprises a generally forward side 81, a generally rearward side 82, a generally upward or top side 83 (e.g., toward the crown of a wearer's head), and a generally bottom side 84 (e.g., toward the wearer's neck). Main body 20 comprises a generally forward-facing portion that comprises an optically-transmissive window 2. In some embodiments, optically-transmissive window 2 may take the form of a through-opening; in other embodiments, it may have one or more transparent panes mounted therein.

Automatic darkening filter apparatus 10 may be mounted in protective headgear 1 (removably or permanently) in any suitable manner. In whatever manner, automatic darkening filter apparatus 10 is mounted in headgear 1 so that an optical-filtering lens 11 is aligned with at least a portion of window 2 so that lens 11 can filter electromagnetic radiation (e.g., visible light, ultraviolet radiation, infrared radiation, etc.) that passes through window 2. That is, lens 11 is positioned within protective headgear 1 so that any electromagnetic radiation that reaches the eyes of a person wearing the headgear must first pass through lens 11 and so may be optically filtered in any desired manner. Often, lens 11 is positioned so that it is directly in front of the wearer's eyes when the protective headgear is worn by a user. If desired, lens 11 may be conveniently located rearward of one or more transparent panes of window 2, e.g. in order to protect lens 11 from damage or debris.

Figure 2:
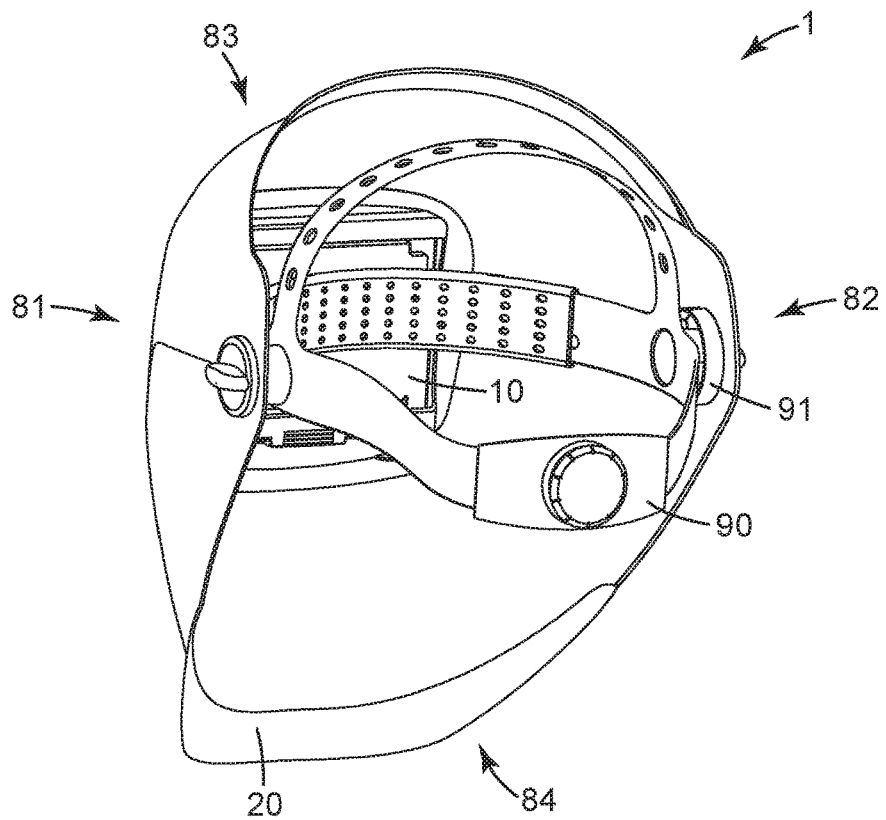
FIG. 2 is a rear-side perspective view of the exemplary protective headgear and automatic darkening filter of FIG. 1.

For clarity of description, the following terminology is used: with window 2 as a reference location, terms such as front, forward, etc. refer to a direction that is toward a source of electromagnetic radiation when headgear 1 is in use (thus for example, FIG. 1 is a view from the front side of headgear 1). Terms such as rear, rearward, etc., refer to a direction that is generally away from the front direction. The rear side of headgear 1 is thus the side that is configured to accept and optically shield at least a portion of a user's head (thus, FIG. 2 is a view from the rear side of headgear 1). These two directions thus combine to establish a forward-rearward axis and direction relative to window 2 of headgear 1.

In some embodiments, protective headgear 1 may comprise a suspension 90, which may be attached to protective headgear 1 by an attachment mechanism 91, as shown e.g. in FIG. 2. Any such suspension may be used, and may comprise any suitable combination of e.g. brow bands, crown bands, occipital bands, and so on. In addition to such a suspension, one or more pads may be provided e.g. on the underside of the crown portion of headgear 1, which pads may serve a protective and/or cushioning function.

Protective headgear 1 may be used e.g. in connection with industrial operations, for example welding (e.g. arc welding, torch welding, acetylene welding), cutting (e.g. laser cutting, acetylene cutting), brazing, soldering, grinding, and the like. It may also be used in connection with medical procedures involving high intensity light (e.g. laser surgery, hair removal, tattoo removal, light-curing of dental resins, etc.). Many other uses are possible.

Automatic darkening filter 10, and lens 11 thereof, may comprise any suitable layer or layers that, individually or collectively, are capable of suitably intercepting, blocking, filtering, etc., electromagnetic radiation. For example, automatic darkening filter 10 may be capable of reducing high-intensity light as encountered in welding operations, to an intensity that is acceptable to a wearer of protective headgear 1. Regardless of the specific design, lens 11 of automatic darkening filter 10 will include a switchable shutter 12 that is capable of controllably blocking electromagnetic radiation. That is, shutter 12 can switch between at least a light state (in which is it relatively highly light-transmissive) and a dark state (in which it is relatively non-transmissive to light). In some embodiments, shutter 12 can also switch into at least one intermediate state that exhibits a light transmissivity in between that of the light state and the dark state. In specific embodiments, shutter 12 can switch into any of a multiplicity of intermediate states between the light state and the dark state. (Here and elsewhere herein, by "state" is meant a condition of relative light-transmissivity, or opacity, of a shutter 12 of lens 11.)

The amount of incident light transmitted by shutter 12 in the various states can be characterized in various ways. One way commonly used in the art is the visible light transmission of the shutter. In various embodiments, shutter 12 is configured so as to exhibit a visible light transmission of less than about 0.5%, less than about 0.1%, or less than about 0.05%, when in a dark state; and, to exhibit a visible light transmission of greater than about 10%, greater than about 20%, or greater than about 50%, when in a light state. In various embodiments the visible light transmission of shutter 12 when in an intermediate state may be less than about 10%, less than about 5%, or less than about 2%, and may be greater than about 0.5%, greater than about 1%, or greater than about 1.5%. Other ranges are possible.

Performance of shutter 12 may also be characterized by a Shade Number which is also commonly known in the art. Thus, in various embodiments shutter 12 may exhibit a Shade Number of e.g. about 9, 10, 11, 12, or 13 when in a dark state. In specific embodiments, shutter 12 may exhibit a Shade Number of about 13 when in a dark state. In some embodiments the Shade Number of the dark state may be a predetermined, single shade number (e.g., a factory pre-set) of 9, 10, 11, 12 or 13). In other embodiments the Shade Number of the dark state may be set as desired by the user (e.g., to a value of 9, 10, 11, 12 or 13).

In various embodiments, shutter 12 may exhibit a Shade Number of less than about 5, less than about 4, or less than about 3, when in a clear state. As noted above, in some embodiments shutter 12 may be able to be set (automatically by shutter control system 16 rather than manually by a user) to an intermediate state that is between a light state and the darkest state attainable by shutter 12. In various embodiments, the Shade Number of shutter 12 when in an intermediate state may be e.g. 6, 7, 8, 9, 10, 11 or 12. (The ordinary artisan will appreciate that the description of a shutter that can reach a darkest state of e.g. Shade Number 13, but can also be set to a state of e.g. Shade Number 10, 11, or 12, may be equivalently thought of as a shutter that can reach a dark state and a variety of intermediate states; or, as a shutter that can reach a variety of dark states.)

Switchable shutter 12 may comprise e.g. one or more liquid crystal layers, polarizing filters, electrochromic materials, and so on. Such components can be configured to exhibit variably controllable transmissivity to radiation (e.g., light), as is well known to those of ordinary skill. If desired, other components (e.g. additives within layers of the shutter, and/or separate layers in the light path) may be provided that constantly block (whether by absorption, reflection, scattering, or some other mechanism) radiation of various wavelengths to a desired degree. For example, one or more of e.g. ultraviolet-blocking coatings, infrared-blocking coatings, interference filters, and the like, may be provided as part of lens 11 of automatic darkening filter 10.

Figure 3:
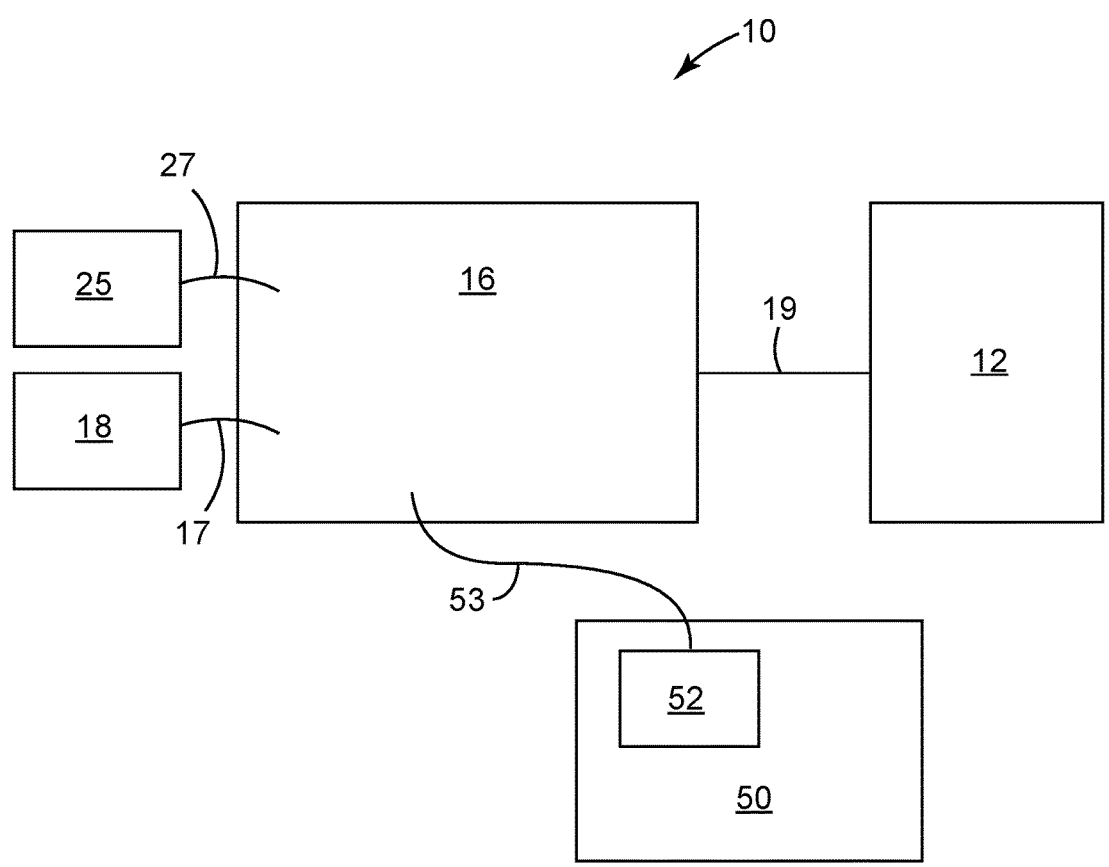
FIG. 3 is a block diagram of one embodiment of an automatic darkening filter apparatus.

With reference to the block diagram of FIG. 3, automatic darkening filter apparatus 10 comprises a shutter control system 16 that is controllably connected to switchable shutter 12. By controllably connected is meant that shutter control system 16 can at least send control signals (orders) to shutter 12 to assume any desired state (e.g., light, dark, intermediate, and so on). Two-way communication between control system 16 and shutter 12 is possible if desired; e.g. shutter 12 may be configured to send update or confirmation signals regarding the particular state of the shutter at any given time. Shutter control system 16 can switch shutter 12 between various states by the use of any convenient control signal; for example, by varying a voltage that is applied to shutter 12. Upon a change in a control signal being applied by shutter control system 16, shutter 12 may often exhibit a response time in lighter-to-darker transitions of less than one millisecond, and a response time in darker-to-lighter transitions of around a few milliseconds. When a constant value of a control signal is applied, shutter 12 typically exhibits a relatively constant light transmission.

Shutter control system 16 is receivably connected to at least one light sensor 18 that can receive light and quantitatively assess the intensity of that light. By receivably connected is meant that control system 16 is configured to at least receive a first signal from light sensor 18. As shown in FIG. 1, light sensor 18 is oriented so that it faces forward; specifically, so that it senses light intensity from the "work view". By work view is meant the approximate area visible to the user of headgear 1 through lens 11. The work view thus not only includes any high-intensity light emission (e.g., spot) from the workpiece being worked upon, it may also include other portions of the workpiece (that are not emitting high-intensity light), and a small or large background area surrounding the workpiece. These factors of course may depend e.g. on how close headgear 1 is to the workpiece. Light sensor 18 thus senses the total light intensity that originates from the work view during ordinary use of headgear 1, and sends a signal that is representative of this total light intensity, to shutter control system 16.

In some embodiments light sensor 18 is located (e.g. as shown in exemplary embodiment FIG. 1) so that it monitors light that has not passed through lens 11. In other embodiments, light sensor 18 may be located rearward of lens 11 so that it monitors light that has passed through lens 11. Such an arrangement (which may be particularly convenient if automatic darkening filter comprises a separate light detector 28, which monitors light that has not passed through lens 11) may advantageously allow enhanced control of the transmitted light levels (and may also allow the use of a light sensor that has a relatively small dynamic range).

In some embodiments, light sensor 18 is capable of sensing at least two levels of light—light above a predetermined threshold intensity, and light below a predetermined threshold intensity. In the simplest version of this, light sensor 18 may be configured to detect only light above a certain predetermined intensity; in such case, light below this intensity is sensed negatively (by the absence of light above this intensity). In other embodiments, light sensor 18 may be capable of sensing multiple levels, e.g. a continuum, of light intensity.

As noted, light sensor 18 is also capable of communicating the detection of some level (intensity) of light to shutter control system 16. In various embodiments, light sensor 18 may be located physically close to some or all of the other components (hardware, etc.) of shutter control system 16 or may be located physically remote from some or all of the other components. Regardless, light sensor 18 is in communication with other components of system 16 via connection 17 (which may be a dedicated wire, an optical fiber, a wireless connection, etc.), as needed for functioning of system 16. It may be preferential to locate light sensor 18 in close proximity to lens 11, so that sensor 18 gathers light from an area that closely approximates the work view of lens 11.

In various embodiments, light sensor 18 may be e.g. a photosensitive device, including but not limited to a photodiode, phototransistor, and so on). In various embodiments, light sensor 18 may be configured to sense light continuously, or intermittently. Similarly, the first signal may be sent to shutter control system 16 continuously, or intermittently. If intermittent monitoring and/or signal transmission is utilized it is preferably done at sufficiently high frequency to enable sufficiently rapid response of shutter 12.

A first signal is generated (either directly by light sensor 18, or by any ancillary microprocessor or the like that is connected thereto) that is representative of the total light intensity originating from the work view. Light sensor 18 is configured to communicate the first signal to shutter control system 16 (whether directly, or through any intermediary processor). Shutter control system 16 is configured to receive this first signal from light sensor 18 (whether directly, or indirectly through some intermediary processor) and to use this signal at least in part to determine an appropriate state of lightness or darkness to control shutter 12 to.

Shutter control system 16 is receivably connected to at least one image acquisition device 25. By receivably connected is meant that control system 16 is configured to receive a second signal from device 25. As shown in FIG. 1, device 25 is oriented so that it faces forward; specifically, so that it acquires an image that is at least substantially corresponds to the work view that sensor 18 senses the overall light intensity level from. Again, this work view not only any high-intensity light emission (e.g., spot) from the workpiece being worked upon, it may also include other portions of the workpiece (that are not emitting high-intensity light), and a small or large background area surrounding the workpiece. In some embodiments image acquisition device 25 is located (e.g. as shown in exemplary embodiment FIG. 1) so that it monitors light that has not passed through lens 11. In other embodiments, image acquisition device 25 may be located rearward of lens 11 so that it monitors light that has passed through lens 11.

From this image, a second signal is generated (either directly by image acquisition device 25, or by any ancillary microprocessor or the like that is connected thereto) that is representative of the area distribution of light intensity within the work view. That is, each area of the work view that is depicted on the image (e.g., in one or more pixels), carries information regarding the intensity of light in that area as imaged, with e.g. areas of higher light intensity and areas of lower light intensity being present over the length and breadth of the work view. By way of specific example, the second signal may carry information representative of the size of an area of high-intensity-light that is emitted from the workpiece (e.g., the welding "spot"), in comparison to the size of the entire work view. Or, it may be representative of the difference in intensity (e.g., the contrast) between the high-light-intensity-spot and background portions of the work view. Or, it may be representative of the differences in light intensity in different areas of the background portion of the work view. In some embodiments, the second signal may be a multiparameter signal that carries information regarding more than one of these topics.

Image acquisition device 25 is configured to communicate second signal to shutter control system 16 (whether directly, or through any intermediary processor). Shutter control system 16 is configured to receive this second signal from image acquisition device 25 (whether directly, or indirectly through some intermediary processor) and to use this signal at least in part to determine an appropriate state of lightness or darkness to control shutter 12 to.

In various embodiments, image acquisition device 25 may be located physically close to some or all of the other components of shutter control system 16 or may be located physically remote from some or all of the other components. Regardless, image acquisition device 25 is in communication with other components of system 16 via connection 27 (which may be a dedicated wire, an optical fiber, a wireless connection, etc.), as needed for functioning of shutter control system 16. It may be preferential to locate image acquisition device 25 in close proximity to shutter 12, so that device 25 images an area that closely approximates the work view of lens 11.

Image acquisition device 25 may be of any suitable device (e.g., camera) that can acceptably acquire an image of the work view. For example, it might comprise one or more CMOS image sensors, charge-coupled devices (CCDs), or the like, so that e.g. a digital image may be generated without the need to perform analog-to-digital conversion. The wavelength range over which a sensor is most sensitive to light may be chosen appropriately. In many embodiments, an array (e.g., a solid-state array) of such sensors may be used in combination to serve collectively as device 25. In various embodiments, image acquisition device 25 may be configured to acquire images continuously, or intermittently. Similarly, the second signal may be sent to control system 16 continuously, or intermittently. If intermittent monitoring and/or signal transmission is utilized, it is preferably done at sufficiently high frequency to enable sufficiently rapid response of shutter 12.

Although if desired the image acquired by device 25 may be e.g. a color map, in many embodiments it may be convenient that it be a greyscale image. That is, the value of each pixel will be a single sample, carrying only intensity information (rather than also carrying color information). Any suitable image processing (e.g. spatial filtering, thresholding, edge enhancement, contrast enhancement, temporal filtering, and so on) may be performed if deemed useful to enhance the usefulness of the second signal. It will be clear to the ordinary artisan that the image(s) that are acquired by image acquisition device 25 are not, in ordinary use of headgear 1, displayed for, or visible to, the person who is wearing the headgear. Rather, the user will visualize the work view through lens 11/window 2, in the customary manner.

As noted, the second signal, derived from the image acquired from image acquisition device 25, will be representative of the area distribution of light intensity over an image of the work view. For example, the second signal may be representative of the difference in the intensity of light in two (or more) different areas of the work view. (By way of specific example, it may represent the difference in intensity of light emitted from a workpiece, from that of a portion of a background area of the work view.) In many embodiments, the information in this signal may be conveniently provided in the form of a ratio (e.g., of light intensity in a first area of the work view to light intensity in a second area of the work view). The ordinary artisan will understand that, in at least some embodiments, the intensity of light emitted from a welding "spot" of a workpiece being worked on, may be vastly higher than that of a background area, e.g., by a factor of $10^3$, $10^4$, $10^5$, $10^6$, or more. Processing the information in a ratioed manner may thus allow intensities over wide dynamic range to be handled; this may also be advantageous in view of the fact that the human visual system has a wide dynamic range and is extremely sensitive to contrast (e.g., the ratio of one intensity to another).

Shutter control system 16 will receive the first signal (indicative of total light intensity in the work view, irrespective of any variations in the light intensity over the work view, the spot size, etc.) and the second signal (obtained from an image that approximates the work view and that is indicative of e.g. variations in light intensity over the work view). Shutter control system 16 may use both of these signals in controlling shutter 12. This may be done in any suitable manner. For example, shutter control system 16 may have one or more microprocessors that receive the first and second signals and process them according to a pre-defined algorithm (or, e.g., a look-up table) in order to chose an appropriate control signal to be sent to shutter 12.

In the special case that the first signal indicates that the light intensity sensed by light sensor 18 is sufficiently low, shutter control system 16 may control shutter 12 to a light (e.g., the lightest possible, i.e. least opaque) state, regardless of the second signal. In fact, in such a case shutter control system 16 may thus ignore the second signal or even reject the second signal from even being received. In another special case in which the first signal indicates that the light intensity sensed by light sensor 18 is sufficiently high, shutter control system 16 may control shutter 12 to a dark (e.g., the darkest possible, i.e. most opaque) state, again regardless of the second signal. Again in such a case, shutter control system 16 may thus ignore the second signal or even reject the second signal from even being received. However, regardless of these special cases, it is emphasized that in ordinary operation of automatic darkening filter 10, shutter control system is configured to receive second signals from image acquisition device 25, whether or not it chooses to actually receive, or act on, those signals.

In many situations in which the light intensity as sensed by light sensor 18 is in between the above two extreme values, the second signal, from the image acquisition device 25, will be considered in reaching the choice of an appropriate state to control shutter 12 to. Thus, the signal received from image acquisition device 25 may allow the state of shutter 12 to be e.g. fine-tuned to a degree not possible when only making use of a single signal indicative of the overall light intensity. This may advantageously enhance the viewing comfort experienced by the user of the protective headgear. For example, shutter 12 may be operated at least slightly differently for a welding operation that is occurring in a dark room, versus one that is occurring outside on a sunny day (even though the intensity of the light that is emitted from the workpiece may be similar in both cases).

As shown in FIG. 1, light sensor 18 and image acquisition device 25 may be conveniently located in a forward-facing side of headgear 1. If desired, one or both of these devices may be e.g. slightly recessed within an aperture of e.g. a forward-facing wall of main body 20 of headgear 1; or they may have a shroud, louver, or any other structure that will cause the field of view of the sensor (or the image acquisition device) to closely approximate the above-discussed work view. In at least some embodiments, light sensor 18 and image acquisition device 25 are separate entities; that is, light sensor 18 is not an image acquisition device, and vice versa.

Shutter control system 16 (and automatic darkening filter 10 in general) can comprise (in addition to a light sensor 18 and an image acquisition device 25) various hardware, electronic, software and/or firmware components, integrated circuits, power sources, etc., as are needed to fully carry out the functioning of shutter control system 16, the light source and image acquisition device, and so on. It will be clear to the ordinary artisan that shutter control system 16 and automatic darkening filter 10 can comprise any electronic components or components (e.g., one or more of resistors, amplifiers, inverters, and so on) as needed for functioning. As is customary, many of these may be provided e.g. in solid state form. In various embodiments, shutter control system 16 may be located close to shutter 12 (e.g., contained in the same physical casing or housing); alternatively, shutter control system 16 may be located physically remote from shutter 12. In either case, shutter control system 16 is operatively connected to shutter 12 via connection 19, which may be a dedicated wire, an optical fiber, a wireless connection, etc.

If desired, in some embodiments, automatic darkening filter apparatus 10 comprises at least one light detector 28 to which shutter control system 16 is receivably connected. Light detector 28 may serve to detect the presence or absence of high-intensity light (e.g., to determine whether or not an operation such as welding is taking place), rather than to quantitatively detect the total light intensity that originates from the work view. Light detector 28 can take the form of any suitable detector, e.g. a photodiode or the like, that is e.g. able to detect light above a predetermined threshold intensity. In some embodiments, light detector 28 may be configured to detect the presence of "flickering" light, whether instead of, or as an adjunct to, the detection of light above a predetermined threshold intensity. (The ordinary artisan will appreciate that such "flickering" light is often a characteristic feature of e.g. welding operations.)

In some embodiments, light detector 28 may be a separate device from light sensor 18 (as shown in exemplary embodiment in FIG. 1). However, in some embodiments a single detecting/sensing device photodiode may be used e.g. in a configuration in which it initially serves to detect and report the presence or absence of high-intensity light, after which (e.g. upon receiving instructions from shutter control system 16) it shifts to a quantitative mode of operation in which it senses the total light intensity that originates from a work view. In at least some embodiments light detector 28 is located (e.g. as shown in exemplary embodiment FIG. 1) so that it monitors light that has not passed through lens 11.

Regardless of the specific method of operation, light detector 28 may serve to provide an initial indication (signal) to shutter control system 16 that e.g. welding is taking place, so that shutter control system 16 may then activate light sensor 18 to function as described in detail earlier herein.

If desired, in some embodiments shutter control system 16 can be in communication with a (potentially) light-emitting device 50 (e.g., a welding unit) and can be capable of receiving an "operating" signal from device 50 that indicates that device 50 is in a condition (e.g., powered) that is likely to emit high light intensity. Such an operating signal may take the form of any signal sent via connection 53 (whether a dedicated wire, an optical fiber, a wireless connection, an IR signal, a radiofrequency broadcast, and the like) that can be received by shutter control system 16 and that indicates that device 50 is in a condition that is likely to emit high light intensity. In such an arrangement, light emitting device 50 may include communication unit 52 that is capable of performing such communication with control system 16 via connection 53. If desired, such an arrangement can include a provision for two-way communication such that device 50 can receive an acknowledgement from automatic darkening filter apparatus 10 that apparatus 10 is functioning, prior to device 50 emitting light. Regardless of the specific mode of operation, the reception of an operating signal by shutter control system 16 may provide an indication to shutter control system 16 that e.g. welding is likely to begin, so that shutter control system 16 may then activate light sensor 18 (and/or light detector 28) to function as described earlier herein.

In some embodiments, automatic darkening filter 10, including shutter control system 16, light sensor 18 and image acquisition device 25, a power source if desired, and so on, can be provided in the form of a cartridge that is removably mountable into protective headgear 1. Such configurations are discussed in detail in U.S. Patent Application Publication No. 20140215673 to Lilenthal, which is incorporated by reference herein in its entirety.

LIST OF EXEMPLARY EMBODIMENTS

Embodiment 1 is an automatic darkening filter apparatus comprising: a switchable shutter capable of assuming at least a dark state and a light state; a shutter control system that is controllably connected to the shutter and that is receivably connected to a light sensor and to an imaging acquisition device, wherein the shutter control system is configured to receive a first signal from the light sensor and a second signal from the image acquisition device, and to use the first signal and the second signal in combination to choose a state to which the switchable shutter is controlled, wherein the first signal is representative of total light intensity that originates from a work view, and wherein the second signal is representative of an area distribution of light intensity within an image of the work view; and wherein the automatic darkening filter apparatus is configured to be mounted in a forward-facing optically transmissive window of a protective headgear.

Embodiment 2 is the automatic darkening filter apparatus of embodiment 1 wherein the switchable shutter is capable of assuming at least one intermediate state that is between the dark state and the light state. Embodiment 3 is the automatic darkening filter apparatus of any of embodiments 1-2 wherein the switchable shutter is capable of assuming any intermediate state over a continuum of intermediate states in between the dark state and the light state. Embodiment 4 is the automatic darkening filter apparatus of any of embodiments 1-3 wherein the light sensor is capable of sensing a continuum of light intensities. Embodiment 5 is the automatic darkening filter apparatus of any of embodiments 1-4 wherein the protective headgear is a welding helmet, shield, or visor. Embodiment 6 is the automatic darkening filter apparatus of any of embodiments 1-5 wherein the automatic darkening filter apparatus is in the form of a cartridge that is removably mountable in the forward-facing optically transmissive window of the protective headgear. Embodiment 7 is the automatic darkening filter apparatus of any of embodiments 1-6 wherein the automatic darkening filter apparatus further comprises at least one light detector. Embodiment 8 is a protective headgear comprising the automatic darkening filter apparatus of any of embodiments 1-7 mounted in a forward-facing optically transmissive window of the protective headgear. Embodiment 9 is the protective headgear of embodiment 8 wherein the image of the work view is a greyscale image that is not displayed for, or visible to, a wearer of the protective headgear. Embodiment 10 is the protective headgear of embodiment 8 wherein the protective headgear is a welding helmet, shield, or visor.

Embodiment 11 is a method for controlling a switchable shutter capable of assuming at least a dark state and a light state, the method comprising: receiving a first signal that is representative of total light intensity that originates from a work view; receiving a second signal that is representative of an area distribution of light intensity over the work view; and, using the first signal and the second signal in combination to choose a state to which a switchable shutter is controlled. Embodiment 12 is the method of embodiment 11 wherein the first signal is received from a light sensor and wherein the second signal is received from an image acquisition device that acquires an image of the work view and that transmits a second signal that is representative of the area distribution of light intensity over the image of the work view. Embodiment 13 is the method of any of embodiments 11-12 wherein the second signal is representative of at least a size of an area of high-intensity light that is emitted from a workpiece in the work view, in comparison to the size of the work view. Embodiment 14 is the method of any of embodiments 11-12 wherein the second signal is representative of a ratio of a light intensity of an area of high-intensity light that is emitted from a workpiece in the work view, to a light intensity of at least a portion of a background area of the work view. Embodiment 15 is the method of any of embodiments 11-12 wherein the second signal is representative of a ratio of a light intensity of a first area of a background portion of the work view, to a light intensity of a second area of the background portion of the work view. Embodiment 16 is the method of any of embodiments 11-12 wherein the second signal is a multiparameter signal that is representative of at least a size of an area of high-intensity light that is emitted from a workpiece in the work view, in comparison to the size of the work view; and, is also representative of a ratio of a light intensity of an area of high-intensity light that is emitted from a workpiece in the work view, to a light intensity of at least a portion of a background area of the work view. Embodiment 17 is the method of any of embodiments 11-16 wherein the method is carried out as part of a welding procedure. Embodiment 18 is the method of any of embodiments 11-17 wherein the method comprises an initial step of receiving a signal from a light detector, which signal indicates that high-intensity light is present in the work view. Embodiment 19 is the method of any of embodiments 11-17 wherein the method uses the automatic darkening filter apparatus of any of embodiments 1-7. Embodiment 20 is the method of any of embodiments 11-17 wherein the method uses the protective headgear of any of embodiments 8-10.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document incorporated by reference herein, this specification as written will control.

What is claimed is:

1. An automatic darkening filter apparatus comprising:
a switchable shutter capable of assuming at least a dark state and a light state;
a shutter control system that is controllably connected to the shutter and that is receivably connected to a light sensor and to an image acquisition device,
wherein the shutter control system is configured to receive a first signal from the light sensor and a second signal from the image acquisition device, and to use the first signal and the second signal in combination to choose a state to which the switchable shutter is controlled,
wherein the first signal is representative of total light intensity that originates from a work view, and wherein the second signal is representative of an area distribution of light intensity within an image of the work view;
and wherein the automatic darkening filter apparatus is configured to be mounted in a forward-facing optically transmissive window of a protective headgear.

2. The automatic darkening filter apparatus of claim 1 wherein the switchable shutter is capable of assuming at least one intermediate state that is between the dark state and the light state.

3. The automatic darkening filter apparatus of claim 1 wherein the switchable shutter is capable of assuming any intermediate state over a continuum of intermediate states in between the dark state and the light state.

4. The automatic darkening filter apparatus of claim 1 wherein the light sensor is capable of sensing a continuum of light intensities.

5. The automatic darkening filter apparatus of claim 1 wherein the protective headgear is a welding helmet, shield, or visor.

6. The automatic darkening filter apparatus of claim 1 wherein the automatic darkening filter apparatus is in the form of a cartridge that is removably mountable in the forward-facing optically transmissive window of the protective headgear.

7. The automatic darkening filter apparatus of claim 1 wherein the automatic darkening filter apparatus further comprises at least one light detector.

8. A protective headgear comprising:
an automatic darkening filter apparatus mounted in a forward-facing optically transmissive window of the protective headgear, the automatic darkening filter comprising,
a switchable shutter capable of assuming at least a dark state and a light state;
a shutter control system that is controllably connected to the shutter and that is receivably connected to a light sensor and to an image acquisition device;
wherein the shutter control system is configured to receive a first signal from the light sensor and a second signal from the image acquisition device, and to use the first signal and the second signal in combination to choose a state to which the switchable shutter is controlled;
wherein the first signal is representative of total light intensity that originates from a work view, and wherein the second signal is representative of an area distribution of light intensity within an image of the work view.

9. The protective headgear of claim 8 wherein the image of the work view is a greyscale image that is not displayed for, or visible to, a wearer of the protective headgear.

10. The protective headgear of claim 8 wherein the protective headgear is a welding helmet, shield, or visor.

11. The protective headgear of claim 8 wherein the automatic darkening filter apparatus is in the form of a cartridge that is removably mounted in the forward-facing optically transmissive window of the protective headgear.

12. The protective headgear of claim 8 wherein the automatic darkening filter apparatus further comprises at least one light detector.

13. A method for controlling a switchable shutter capable of assuming at least a dark state and a light state, the method comprising:
receiving a first signal that is representative of total light intensity that originates from a work view;
receiving a second signal that is representative of an area distribution of light intensity over the work view;
and, using the first signal and the second signal in combination to choose a state to which a switchable shutter is controlled.

14. The method of claim 13 wherein the first signal is received from a light sensor and wherein the second signal is received from an image acquisition device that acquires an image of the work view and that transmits a second signal that is representative of the area distribution of light intensity over the image of the work view.

15. The method of claim 13 wherein the second signal is representative of at least a size of an area of high-intensity light that is emitted from a workpiece in the work view, in comparison to the size of the work view.

16. The method of claim 13 wherein the second signal is representative of a ratio of a light intensity of an area of high-intensity light that is emitted from a workpiece in the work view, to a light intensity of at least a portion of a background area of the work view.

17. The method of claim 13 wherein the second signal is representative of a ratio of a light intensity of a first area of a background portion of the work view, to a light intensity of a second area of the background portion of the work view.

18. The method of claim 13 wherein the second signal is a multiparameter signal that is representative of at least a size of an area of high-intensity light that is emitted from a workpiece in the work view, in comparison to the size of the work view; and, is also representative of a ratio of a light intensity of an area of high-intensity light that is emitted from a workpiece in the work view, to a light intensity of at least a portion of a background area of the work view.

19. The method of claim 13 wherein the method is carried out as part of a welding procedure.

20. The method of claim 13 wherein the method comprises an initial step of receiving a signal from a light detector, which signal indicates that high-intensity light is present in the work view.

* * * * *